(12) United States Patent
Fischer et al.

(10) Patent No.: US 7,064,239 B2
(45) Date of Patent: Jun. 20, 2006

(54) PREPARATION OF 1,6-HEXANEDIOL

(75) Inventors: Rolf-Hartmuth Fischer, Heidelberg (DE); Thomas Krug, Worms (DE); Andrea Haunert, Mannheim (DE); Michael Röper, Wachenheim (DE); Tilman Sirch, Schifferstadt (DE); Wolfram Stüer, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/537,829

(22) PCT Filed: Dec. 3, 2003

(86) PCT No.: PCT/EP03/13634

§ 371 (c)(1),
(2), (4) Date: Jun. 8, 2005

(87) PCT Pub. No.: WO2004/054948

PCT Pub. Date: Jul. 1, 2004

(65) Prior Publication Data

US 2006/0014988 A1 Jan. 19, 2006

(30) Foreign Application Priority Data

Dec. 13, 2002 (DE) .................. 102 58 316

(51) Int. Cl.
*C07C 31/20* (2006.01)
*C07C 31/18* (2006.01)

(52) U.S. Cl. .................. 568/864; 568/852; 568/861

(58) Field of Classification Search .......... 568/864, 568/861, 852
See application file for complete search history.

(56) References Cited

FOREIGN PATENT DOCUMENTS

| EP | 0 552 463 A1 | 12/1991 |
| EP | 0 475 386 A2 | 3/1992 |
| EP | 0 475 386 B1 | 8/1995 |
| JP | A 06 329 567 | 11/1994 |

OTHER PUBLICATIONS

Houbeu-Wegl, Methodeu de Organ. Chemie Baud IV ; 1980 Sateu 45-67 Iud Sateu 16-26.
Moseley, et al., Pentamethylcyclopentadienyl-rhodium and -iridium Halides. Part II. Reactions with Mono-, Di, and Tri-olefins; J. American. Chem. Soc., 1970, pp. 2875-2883.
M. Brookhart,et al., A Convenient Reagent for Generation and Stabilization of Cationic, Highly Electrophilic Organometallic Complexes: American Chemical Society:pp. 3920-3922, vol. 11, No. 11, 1992.
Brookhart, et al., Catalytic Tail-to-Tail Dimerization of Methyl Acrylate Using Rh(III) Catalysts; J. American Chemistry Society;1991, 113,pp. 2777-2779.

*Primary Examiner*—Elvis O. Price
(74) *Attorney, Agent, or Firm*—Connolly Bove Lodge & Hutz LLP; Matthew J. Mason

(57) ABSTRACT

The present invention provides a process for preparing 1,6-hexanediol having a purity of ≧99.5% by weight by catalytically dimerizing acrylic esters and catalytically hydrogenating the hexenedioic diesters obtained in this way to 1,6-hexanediol by a) dimerizing $C_1$- to $C_8$-acrylic esters in the presence of at least one rhodium compound to give mixtures of predominantly 2- and 3-hexenedioic diesters, b) hydrogenating the resulting dimerizing effluent in the presence of chromium-free catalysts comprising predominantly copper as the hydrogenation component and c) purifying the crude 1,6-hexanediol obtained in this way by fractional distillation.

16 Claims, No Drawings

PREPARATION OF 1,6-HEXANEDIOL

CROSS REFERENCE TO RELATED APPLICATION

The present application is a National Stage application of PCT/EP2003/013634, filed Dec. 3, 2003, which claims priority from German Patent Application No. DE 102 58 316.1, filed Dec. 13, 2002.

The present application relates to a process for preparing 1,6-hexanediol of high purity by dimerizing acrylic esters in the presence of rhodium catalysts, optionally removing unconverted acrylic esters, hydrogenating the dimerization effluents obtained in this way in the presence of catalysts comprising predominantly copper and distillatively purifying the 1,6-hexanediol obtained to a purity of at least 99.5%.

The preparation of 1,6-hexanediol by catalytic hydrogenation of $C_6$ compounds such as adipic acid or adipic diesters is known. The linear dimerization of acrylic esters opens up an alternative route to hexanediol based on a C3 raw material source. For instance, the methyl acrylate starting compound required for the dimerization can be prepared by oxidation of propane or propene to acrylic acid and subsequent esterification with methanol.

Processes for preparing dimethyl hexenedioates starting from methyl acrylate are known per se. Numerous catalysts have been described in the literature. The transition metals Ru, Rh, Ni and Pd have thus for proven to be catalytically active.

For the rhodium catalysts, it was possible to prepare a number of active and selective catalyst systems starting from $RhCl_3$ by varying the ligands.

EP-A 475 368 describes the dimerization of acrylic esters such as methyl acrylate in the presence of specific cationic rhodium compounds as catalysts. Isomer mixtures comprising E- and Z-2-hexenedioic diesters and E- and Z-3-hexenedioic diesters are obtained.

Moreover, JP-A 06 329567, Example 1, discloses the conversion of methyl acrylate to dimethyl hexenedioates at 65° C. in the presence of palladium chloride, iron chloride and iron nitrate (acrylic ester conversion 60%). The dimethyl dehydroadipate selectivity after distillative workup was 95%. Diester obtained in this way was dissolved in methanol and hydrogenated at 250° C. in the presence of a copper chromite catalyst for 4 hours. The 1,6-hexanediol yield was 97% (based on dimethyl hexenedioate) and the 1,6-hexanediol selectivity therefore 92% (based on methyl acrylate).

According to JP-A 6 100496, Example 1, the content of nonlinear dimers is 1%.

It is an object of the present invention to provide a process for preparing 1,6-hexanediol in a purity of at least 99.5% starting from acrylic esters. It should be possible to use the dimerization product for the hydrogenation without costly and inconvenient purification, and to achieve high 1,6-hexanediol yields in the hydrogenation. It should be possible to work up the hydrogenation effluent distillatively without great cost and inconvenience to give 1,6-hexanediol in a purity of at least 99.5%.

We have found that this object is achieved by a process for preparing 1,6-hexanediol having a purity of $\geq 99.5\%$ by weight by catalytically dimerizing acrylic esters and catalytically hydrogenating the hexenedioic diesters obtained in this way to 1,6-hexanediol by a) dimerizing $C_1$- to $C_8$-acrylic esters in the presence of at least one rhodium compound to give mixtures of predominantly 2- and 3-hexenedioic diesters, b) hydrogenating the resulting dimerizing effluent in the presence of chromium-free catalysts comprising predominantly copper as the hydrogenation component and c) purifying the crude 1,6-hexanediol obtained in this way by fractional distillation.

Compared to the dimerization with palladium (Pd) catalysts (JP-A 06 329567), the dimerization with rhodium (Rh) catalysts has the advantage that higher acrylic ester conversions and higher yields of linear C6 diesters are achieved. In the case of Pd-catalyzed dimerization, the higher proportion of 2-methyleneglutaric diesters and double bond isomers of these compounds leads after hydrogenation to a higher proportion of 2-methyl-1,5-pentanediol. This is associated with a more costly and inconvenient distillation.

Preference is given to carrying out the acrylic ester dimerization according to EP-A 475 386, whose disclosure content is explicitly incorporated herein, in the presence of cationic rhodium compounds. Useful cationic rhodium compounds are in particular the compounds disclosed in EP-A 475 386 of the type $[L^1RhL^2L^3R]^+X^-$, wherein $L^1$ is an anionic pentahapto ligand;
$L^2$ and $L^3$ are neutral 2-electron donor ligands;
R is selected from the group of H, $C_1$–$C_{10}$-alkyl, $C_6$–$C_{10}$-aryl and $C_7$–$C_{10}$-aralkyl ligands;
$X^-$ is an noncoordinating anion; and wherein two or three of $L^2$, $L^3$ and R are optionally connected. Instead of rhodium, ruthenium complexes can also be used. Useful acrylic esters are aliphatic and cycloaliphatic $C_1$- to $C_8$-esters, for example methyl acrylate, $C_6$- to $C_{10}$-aryl and -heteroaryl esters, for example phenyl acrylate. The two ester radicals may be the same or different. The acrylic ester used with preference is alkyl acrylate, with particular preference methyl acrylate. The reaction is carried out batchwise or continuously at temperatures of from −100 to 150° C. and pressures of from 0.1 to 1 atm.

The reaction mixture is worked up by removing the organic fractions as a mixture from the catalyst without distillative workup of the individual components. When the acrylic ester conversion was not quantitative, it is possible in some cases to remove only the unconverted acrylic ester and either recycle it into the dimerization stage or use it in another way, although preference is given to removing and recycling into the dimerization step.

The dimerization effluent obtained after substantial removal of unconverted acrylic ester consists, in addition to 2-methyleneglutaric diester, 2-methyl-2-pentenedioic diester, adipic diester, acrylic ester and propionic ester, predominantly of E- and Z-2-hexenedioic diester, E- and Z-3-hexenedioic diester.

The dimerization effluent is subjected without further purification to the hydrogenation b), optionally after removing unconverted acrylic ester.

The hydrogenation is effected catalytically either in the gas or liquid phase. Useful catalysts are in principle all homogeneous and heterogeneous catalysts suitable for hydrogenating carbonyl groups, such as metals, metal oxides, metal compounds or mixtures thereof. Examples of homogeneous catalysts are described in H. Kropf, Houben-Weyl, Methoden der Organischen Chemie, Volume IV/1c, Georg Thieme Verlag Stuttgart, 1980, pp. 45 to 67, and examples of heterogeneous catalysts in Houben-Weyl, Methoden der Organischen Chemie, Volume IV/1c, pp. 16 to 26.

Preference is given to using catalysts which comprise one or more of the elements of transition groups I and VI to VIII of the Periodic Table of Elements, preferably copper, chromium, molyb-denum, manganese, rhenium, ruthenium, cobalt, nickel and palladium, more preferably copper, cobalt, nickel or rhenium.

The catalysts may consist of active components alone or the active components may be applied to supports. Examples of suitable support materials are $Cr_2O_3$, $Al_2O_3$, $SiO_2$, $ZrO_2$, ZnO, BaO and MgO or mixtures thereof.

In particular, the catalytically active main constituent of the catalyst is copper oxide. This is applied to an oxidic support. A suitable support material is aluminum oxide whose use is preferred in accordance with one embodiment of the present invention. In another embodiment of the present invention, the support material used is preferably a combination of aluminum oxide with zinc oxide in a weight ratio of from 20:1 to 1:20, preferably from 5:1 to 1:5. The amount of copper oxide is <80% by weight. Preferred catalyst compositions comprise <70% by weight of copper oxide and >30% by weight of support, particularly preferred catalysts from 10 to 65% by weight of copper oxide and from 35 to 90% by weight of support.

Preference is further given to hydrogenation catalysts as described in EP-A 552 463. These are catalysts which in oxidic form have the composition $$Cu_aAl_bZr_cMn_dO_x$$

where a>0, b>0, c≧0, d>0, a>b/2, b>a/4, a>c and a>d, and x is the number of oxygen ions required per formula unit to preserve electronic neutrality. These catalysts can be prepared, for example, according to the details of EP-A 552 463 by precipitating sparingly soluble compounds from solutions which contain the appropriate metal ions in the form of their salts.

Specifically, useful catalysts have, for example, a composition of about 70% by weight of CuO, 20% by weight of $Al_2O_3$ and 10% by weight of $Mn_2O_3$.

Optionally, the hydrogenation catalysts used in accordance with the invention which are Cr-free may comprise one or more further metals or a compound thereof, preferably an oxide, from groups 1 to 14 (IA to VIIIA and IB to IVB of the old IUPAC nomenclature) of the Periodic Table of the Elements. When such a further oxide is used, preference is given to using $TiO_2$, $ZrO_2$, $SiO_2$ and/or MgO.

The catalysts used may additionally comprise an assistant in an amount of from 0 to 10% by weight. In this context, an assistant is an organic or inorganic substance which contributes to improved processing during catalyst preparation and/or to an increase in the mechanical stability of the shaped catalyst bodies. Such assistants are known to those skilled in the art; examples include graphite, stearic acid, silica gel and copper powder.

The catalysts can be prepared by methods known to those skilled in the art. Preferences is given to processes in which the copper oxide is in finely divided form and is intimately mixed with the other constituents, particular preference to precipitation reactions. In such reactions, precursor compounds dissolved in a solvent are precipitated with a precipitating agent in the presence of further metal compounds which are soluble or suspended in the solvent, filtered off, washed, dried and optionally calcined. At this point, reference is once again made explicitly to the disclosure of EP-A 552 463.

These starting materials can be processed by known methods to give the shaped bodies, for example extruding, tableting or by agglomeration processes, optionally with the addition of assistants.

Alternatively, catalysts according to the invention can be prepared, for example, by applying the active component to a support, for example by impregnating or vapor deposition. Catalysts according to the invention can also be obtained by shaping a heterogeneous mixture of active component or precursor compound thereof with a support component or precursor compound thereof.

In the case of hydrogenation according to the invention, the catalyst is used in reduced, activated form. The activation is effected with reducing gases, preferably hydrogen or hydrogen/inert gas mixtures, either before or after installation into the reactor in which the process according to the invention is carried out. When the catalyst has been installed into the reactor in oxidic form, the activation can be carried out either before start-up of the plant with the hydrogenation according to the invention or during the start-up, i.e. in situ. The separate activation before the start-up of the plant is effected generally with reducing gases, preferably hydrogen or hydrogen/inert gas mixtures, at elevated temperatures, preferably between 100 and 300° C. In the case of the in-situ activation, the activation is effected when running up the plant by contact with hydrogen at elevated temperature.

The catalysts are used as shaped bodies. Examples include extrudates, ribbed extrudates, other extrudate shapes, tablets, rings, spheres and spall.

The BET surface area of the copper catalysts in the oxidic state is from 10 to 400 $m^2/g$, preferably from 15 to 200 $m^2/g$, in particular from 20 to 150 $m^2/g$. The copper surface area ($N_2O$ decomposition) of the reduced catalyst in the installed state is >0.2 $m^2/g$, preferably >1 $m^2/g$, in particular >2 $m^2/g$.

The catalysts used in accordance with the invention generally have a sufficient on-stream time. Should the activity and/or selectivity of the catalyst nevertheless fall in the course of the operating time, it can be regenerated by methods known to those skilled in the art. These preferably include reductive treatment of the catalyst in a hydrogen stream at elevated temperature. Optionally, the reductive treatment may be preceded by an oxidative treatment. In this case, the catalyst bed is flowed through by a molecular oxygen-containing gas mixture, for example air, at elevated temperature. There is also the possibility of washing the catalyst with a suitable solvent, for example methanol, THF or gamma-butyrolactone, and subsequently drying it in a gas stream.

Preference is given to using heterogeneous catalysts which are used either as a fixed bed, as a fluidized bed or as a suspension. When the hydrogenation is carried out in the gas phase and over fixed bed catalyst, preference is generally given to using temperatures of from 150 to 300° C. at pressures of from 1 to 80 bar. The amount of hydrogen used as hydrogenating agent and carrier gas is at least sufficient that reactants, intermediates and products never become liquid during the reaction.

When the hydrogenated is effected in the liquid phase with fixed bed or suspended catalyst, it is generally carried out at temperatures between 100 and 350° C., preferably 120 and 300° C., and pressures of from 30 to 350 bar, preferably from 40 to 300 bar.

The hydrogenation can be carried out in one reactor or a plurality of reactors connected in series. The hydrogenation in the liquid phase over a fixed bed can be carried out either by the trickle method or the liquid phase method. In a preferred embodiment, a plurality of reactors is used, in which case the predominant proportion of the ester is hydrogenated in the first reactor and the first reactor is preferably operated with liquid circulation for heat removal and the subsequent reactor or reactors is/are preferably operated without circulation to complete the conversion.

The hydrogenation may be carried out with or without addition of a solvent. Useful solvents include alcohols, ethers, hydrocarbons, for example methanol, isopropanol, ethanol, dioxane, tetrahydrofuran, n-pentane and from 5 to 70%, preferably from 10 to 60%, more preferably from 15 to 50%, solutions of formylvaleric ester isomer mixtures. Particular preference is given to using the alcohol which is also released in the hydrogenation of the ester groups as the solvent.

The hydrogenation may be carried out batchwise, preferably continuously.

The catalyst hourly space velocity is from 0.01 to 1, preferably from 0.05 to 0.8, more preferably from 0.1 to 0.5, kg of $C_6$ diester to be hydrogenated/l of catalyst·hour.

The hydrogen/reactant molar ratio is likewise a parameter which has an important influence on the economic viability of the process according to the invention. From an economic point of view, a low hydrogen/reactant ratio is desirable. The lower limit is at a value of 5, although higher hydrogen/reactant molar ratios of from 20 to 400 are generally employed.

In order to adjust the hydrogen/reactant molar ratios used in accordance with the invention, a portion of the hydrogen is recycled. To this end, the cycle gas compressors known to those in the art are generally used. The amount of hydrogen consumed chemically by the hydrogenation is replaced. In a preferred embodiment, a portion of the cycle gas is discharged, in order to remove inert compounds. The recycled hydrogen can also, optionally after preheating, be used to evaporate the reactant stream.

All products are recycled together with the hydrogen cycle gas which do not or do not completely condense out on cooling of the gas stream leaving the hydrogenation reactor. The cooling temperature is from 0 to 60° C., preferably from 20 to 45° C.

The conversion, based on the sum of $C_6$ diesters forming 1,6-hexanediol is above 95%, in particular above 98%.

The hydrogenation effluent consists substantially of 1,6-hexanediol and the alcohol corresponding to the ester group. A further important constituent is 2-methyl-1,5-pentanediol.

The hydrogenation effluent is purified by fractional distillation in one or more columns.

It could not have been predicted that the hydrogenation of unpurified effluents of acrylic ester dimerization would result in a crude hexanediol which can be purified to above 99.5% by distillation. In particular, it could not have been predicted that it would be possible to move 2-methyl-1,5-pentanediol as an isomer of 1,6-hexanediol with acceptable cost and inconvenience.

The process according to the invention is illustrated by the examples which follow.

EXAMPLE 1

1.1 Dimerization of Methyl Acrylate in the Presence of Rh Catalyst

The experiments were carried out under an atmosphere of dried and repurified argon by means of standard Schlenk techniques. Methylene chloride was dried over $P_2O_5$, methyl acrylate (from Aldrich, stabilized with methoxyphenol) was stored over 4 Å molecular sieve and used without further treatment. The complex $Cp*Rh(C_2H_4)_2$ ($Cp*$=pentamethylcyclopentadienyl) was prepared starting from $[Cp*RhCl_2]_2$ by the method of K. Moseley, J. W. Kang, P. M. Maitlis J. Chem. Soc. (A) 1970, 2875–2883. The starting material $[Cp*RhCl_2]_2$ was synthesized by the method of B. L. Booth, R. N. Haszeldine, M. Hill J. Chem. Soc. (A) 1969, 1299–1303. The acid $HBAr^F_4$ required to activate the catalyst was prepared according to M. Brookhart, B. Grant, A. F. Volpe Organometallics 1992, 11, 3920–3922. $HBAr^F_4$ refers to the bis-etherate of tetrakis[3,5-bis(trifluoromethyl)phenyl]boric acid.

The reaction effluents were analyzed by means of GC (instrument: Hewlett Packard 5820; column: HP-5; length: 30 m; diameter: 0.25 mm; film thickness 1.0 µm), and the structures of the products were assigned by means of GC-MS coupling. All data in area percent.

In a similar manner to Example 14 in EP-A 475 386, 20 mg (0.06 mmol) of $Cp*Rh(C_2H_4)_2$ were admixed in a suitable reaction vessel initially with 80 ml of methyl acrylate and subsequently, at 0° C., with a solution of the stoichiometric amount (based on Rh) of the acid $HBAr^F_4$ in 10 ml of $CH_2Cl_2$. The mixture was heated to 55° C. and stirred under 1 bar of hydrogen for 4 h.

The reaction effluent was then fractionally distilled in order to remove the homogeneously dissolved rhodium catalyst. The first runnings removed at atmospheric pressure were low boilers (methyl acrylate, methyl propionate and methylene chloride).

The main fraction which is used for the subsequent hydrogenation was a mixture of the following composition. The different isomeric dimethyl 2-methylene glutarates and dimethyl hexenedioates are each combined:

| | |
|---|---|
| Methyl acrylate: | 0.15% |
| Methyl propionate: | 0.10% |
| Dimethyl 2-methyleneglutarate and isomers: | 0.52% |
| Dimethyl hexenedioate: | 98.72% |
| Dimethyl adipate: | 0.35% |

Only small amounts of triester and polymer remain in the residue of the distillation.

1.2 Hydrogenation of the Dimerization Effluent Obtained by 1.1

In a batchwise autoclave experiment, a mixture of 30 g of the ester mixture characterized in 1.1 and 70 g of methanol were stirred in the presence of 20 g of copper catalyst (60% of CuO, 30% of $Al_2O_3$, 10% of $Mn_2O_3$) at 210° C./240 bar for 6 hours. The oxidic catalyst was activated with hydrogen at 200° C./300 bar before the hydrogenation.

According to gas chromatography analysis (internal standard: diethylene glycol dimethyl ether), the 1,6-hexanediol yield was 99% (based on linear $C_6$ diesters obtained by 1.1). The crude hydrogenation effluent contained 0.4% of 2-methyl-1,5-pentanediol.

1.3 Distillation of the Hydrogenation Effluent

The distillation of hydrogenation effluent from which methanol had been substantially removed on a spinning band column (max. 160° C./1 mbar) resulted in two main fractions having a 1,6-hexanediol purity of 99.6%. 2-Methyl-1,5-pentanediol was present in only 1000 ppm and 300 ppm respectively.

COMPARATIVE EXAMPLE 1 a) Dimerization according to JP-A 06 329 567 Example 1
0.34 g (2 mmol) of $PdCl_2$, 8.1 g (50 mmol) of $FeCl_3$, 86 g (1 mmol) of methyl acrylate and 2.0 g (5 mmol) of Fe(NO$_3$)$_3$.9 H$_2$O were reacted at 65° C. for 15 h. The catalyst fractions present in solid form after cooling were filtered out of the reaction effluent obtained. The organic phase was worked up by Kugelrohr distillation. Distillation was effected first at 80° C./150 mbar, then at 50 mbar and finally at 1 mbar. This resulted in 35.9 g of unconverted methyl acrylate and 12.4 g of a distillate mixture of linear and branched unsaturated C$_6$-dimethyl dicarboxylates. The 12.5 g distillate mixtures consisted of 84% by weight of linear dimethyl 2- and 3-hexenedioates and 2.4% by weight of dimethyl 2-methyleneglutarate and double bond isomers of this compound. The ratio determined by gas chromatography of linear to branched unsaturated esters was therefore 35:1. The distillation residue obtained was 9 g of solids.

b) Hydrogenation of the mixture of linear and branched C$_6$-dimethyl dicarboxylates 12 g of the mixture obtained by a) of linear and branched C$_6$-dicarboxylic diesters were dissolved in 100 g of methanol and hydrogenated in the presence of 10 g of the copper catalyst described above in inventive Example 1.2, as described there.

After the hydrogenation, it was found that the copper catalyst had turned red and that the 3×3 mm tablets used had completely disintegrated. Gas chromatography analysis of the hydrogenation effluent showed that dimethyl adipate had quite predominantly been formed. Repetition of the experiment leads to the same result.

The results of the comparative example show that the Pd-catalyzed dimerization proceeds with lower acrylic ester conversions and a lower ratio of linear to branched C$_6$ dicarboxylic esters:

Ratio of Linear to Branched C$_6$ dimethyl dicarboxylates

| Rh dimerization: | 190:1 |
| Pd dimerization: | 35:1 |

Since the unsaturated, branched C$_6$ dimethyl dicarboxylates form 2-methyl-1,5-pentanediol in the hydrogenation which has to be removed from the 1,6-hexanediol, 1,6-hexanediol purification, starting from Pd-dimerized crude C$_6$ dimethyl dicarboxylates entails a very complicated distillation. The comparative experiment also shows that the copper hydrogenation catalysts decompose when the diester from the Pd-catalyzed dimerization of acrylic esters is used and that they lose the ability to hydrogenate ester groups.

We claim:

1. A process for preparing 1,6-hexanediol comprising catalytically dimerizing acrylic esters and catalytically hydrogenating the hexenedioic diesters obtained in this way to 1,6-hexanediol by:
   a) dimerizing C$_1$- to C$_8$-acrylic esters in the presence of at least one rhodium compound to give mixtures of predominantly 2- and 3-hexenedioic diesters;
   b) hydrogenating the resulting dimerizing effluent in the presence of chromium-free catalysts comprising predominantly copper as the hydrogenation component; and
   c) purifying the crude 1,6-hexanediol obtained in this way by fractional distillation;
   wherein the 1,6-hexanediol so prepared has a purity of at least 99.5% by weight.

2. The process as claimed in claim 1, wherein unconverted acrylic ester is removed from the dimerization mixture before the hydrogenation.

3. The process as claimed in claim 1, wherein the acrylic ester used is methyl acrylate.

4. The process as claimed in claim 1, wherein the hydrogenation is carried out over a catalyst which in the oxidic form has the composition $$Cu_aAl_bZr_cMn_dO_x$$

where a>0, b>0, c≧0, d>0, a>b/2, b>a/4, a>c and a>d, and x is the number of oxygen atoms required per formula unit to preserve electronic neutrality.

5. The process as claimed in claim 1, wherein the dimerization is carried out at from −100 to 150° C. and at pressures of from 0.1 to 1 atm.

6. The process as claimed in claim 1, wherein the hydrogenation is carried out at from 100 to 350° C. and at pressures of from 30 to 350 bar.

7. The process according to claim 2, wherein the acrylic ester used is methyl acrylate.

8. The process according to claim 2, wherein the hydrogenation is carried out over a catalyst which in the oxidic form has the composition $$Cu_aAl_bZr_cMn_dO_x$$

where a>0, b>0, c≧0, d>0, a>b/2, b>a/4, a>c and a>d, and x is the number of oxygen atoms required per formula unit to preserve electronic neutrality.

9. The process according to claim 3, wherein the hydrogenation is carried out over a catalyst which in the oxidic form has the composition $$Cu_aAl_bZr_cMn_dO_x$$

where a>0, b>0, c≧0, d>0, a>b/2, b>a/4, a>c and a>d, and x is the number of oxygen atoms required per formula unit to preserve electronic neutrality.

10. The process according to claim 2, wherein the dimerization is carried out at from −100 to 150° C. and at pressures of from 0.1 to 1 atm.

11. The process according to claim 3, wherein the dimerization is carried out at from −100 to 150° C. and at pressures of from 0.1 to 1 atm.

12. The process according to claim 4, wherein the dimerization is carried out at from −100 to 150° C. and at pressures of from 0.1 to 1 atm.

13. The process according to claim 2, wherein the hydrogenation is carried out at from 100 to 350° C. and at pressures of from 30 to 350 bar.

14. The process according to claim 3, wherein the hydrogenation is carried out at from 100 to 350° C. and at pressures of from 30 to 350 bar.

15. The process according to claim 4, wherein the hydrogenation is carried out at from 100 to 350° C. and at pressures of from 30 to 350 bar.

16. The process according to claim 5, wherein the hydrogenation is carried out at from 100 to 350° C. and at pressures of from 30 to 350 bar.

* * * * *